US011958046B1

(12) United States Patent
Ranjan et al.

(10) Patent No.: US 11,958,046 B1
(45) Date of Patent: Apr. 16, 2024

(54) METHODS AND SYSTEMS FOR ALKYLATE PRODUCTION INVOLVING A MULTI-ZONE ALKYLATION REACTOR

(71) Applicant: KELLOGG BROWN & ROOT LLC, Houston, TX (US)

(72) Inventors: Rajeev Ranjan, Delhi (IN); Anubhav Kapil, Sugar Land, TX (US)

(73) Assignee: KELLOGG BROWN & ROOT LLC, Houston, TX (US)

( * ) Notice: Subject to any disclaimer, the term of this patent is extended or adjusted under 35 U.S.C. 154(b) by 0 days.

(21) Appl. No.: 18/336,936

(22) Filed: Jun. 16, 2023

(51) Int. Cl.
| | |
|---|---|
| B01J 8/04 | (2006.01) |
| C07C 2/54 | (2006.01) |
| C07C 2/56 | (2006.01) |
| C07C 2/58 | (2006.01) |
| C07C 2/76 | (2006.01) |

(52) U.S. Cl.
CPC ........... B01J 8/0492 (2013.01); B01J 8/0446 (2013.01); C07C 2/76 (2013.01); *B01J 2208/00752* (2013.01); *B01J 2208/00761* (2013.01); *C07C 2/54* (2013.01); *C07C 2/56* (2013.01); *C07C 2/58* (2013.01)

(58) Field of Classification Search
CPC ................ B01J 8/0492; B01J 8/0446; B01J 2208/00752; B01J 2208/00761; C07C 2/76; C07C 2/54; C07C 2/56; C07C 2/58
See application file for complete search history.

(56) References Cited

U.S. PATENT DOCUMENTS

| | | | | |
|---|---|---|---|---|
| 5,817,908 | A * | 10/1998 | Mehlberg | C07C 2/54 585/731 |
| 5,849,976 | A * | 12/1998 | Gosling | B01J 8/12 585/709 |
| 5,856,606 | A * | 1/1999 | Oroskar | C07C 2/58 585/446 |
| 9,079,815 | B2 | 7/2015 | Mukherjee et al. | |
| 10,179,753 | B2 | 1/2019 | Mukherjee et al. | |
| 2011/0152590 | A1* | 6/2011 | Sadler | C07C 2/58 585/312 |
| 2011/0152591 | A1* | 6/2011 | Sadler | C07C 2/58 585/312 |
| 2016/0263547 | A1* | 9/2016 | Mohr | B01J 19/26 |
| 2016/0264494 | A1* | 9/2016 | Mohr | C10G 29/205 |
| 2017/0144141 | A1* | 5/2017 | Lafyatis | B01J 31/0282 |
| 2020/0031733 | A1 | 1/2020 | Mukherjee et al. | |
| 2021/0040013 | A1* | 2/2021 | Levin | C10G 57/005 |
| 2021/0040014 | A1* | 2/2021 | Choudhary | C07C 2/58 |
| 2022/0126252 | A1* | 4/2022 | Dong | B01J 14/00 |

* cited by examiner

Primary Examiner — Ali Z Fadhel
(74) Attorney, Agent, or Firm — Gary M. Machetta

(57) ABSTRACT

Methods and systems for alkylate production involving a multi-zone alkylation reactor. The multi-zone alkylation reactor includes a plurality of alkylation zones spaced vertically in a series configuration and a partition splitting the plurality of alkylation zones into at least two mechanically separated catalytic volumes.

20 Claims, 4 Drawing Sheets

METHODS AND SYSTEMS FOR ALKYLATE PRODUCTION INVOLVING A MULTI-ZONE ALKYLATION REACTOR

TECHNICAL FIELD

The present disclosure relates to embodiments of a multi-zone alkylation reactor and methods of its use in an alkylate production system. These systems and methods can increase the alkylate production and may also reduce the amount of utilized recirculation flow or regenerated gas flow to the alkylation reactor.

BACKGROUND

Refining operations have struggled to meet high demands for higher octane fuels. Technologies, such as KBR's solid acid alkylation technology (K-SAAT™ technology), convert olefins in an alkylation reactor to alkylate using an isobutane solvent. The alkylation process uses a fixed bed catalyst supported reaction to convert the isoparaffin solvent and olefins into higher molecular weight paraffins. In the fixed bed reactor, the primary reaction of olefin with isoparaffin competes with the secondary reaction between the olefins. The rate constant of the secondary, olefin to olefin, reaction is 2 orders of magnitude higher than the rate constant of the primary reaction. As such, the isobutane to olefin (I/O) ratio is desirably kept at least two orders of magnitudes higher. To maintain this relatively high I/O ratio, a large amount of an alkylate-containing stream from the alkylation reactor is recycled back to the alkylation reactor. However, this large recycle and the associated pressure drop decreases the amount of alkylate that could potentially be processed.

SUMMARY OF THE DISCLOSURE

Provided herein are systems and methods to address these shortcomings of the art and provide other additional or alternative advantages. The disclosure herein provides several embodiments of multi-zone alkylation reactors and systems and methods for alkylate production.

An embodiment of an alkylation system includes a multi-zone alkylation reactor. This multi-zone alkylation reactor includes a plurality of alkylation zones spaced vertically in a series configuration. The multi-zone alkylation reactor includes at least one vertical partition splitting the plurality of alkylation zones into at least a first mechanically separated catalytic volume and a second mechanically separated catalytic volume. Additionally, the multi-zone alkylation reactor includes an isobutane inlet positioned to supply an isobutane stream to the first mechanically separated catalytic volume and at least one olefinic feed inlet positioned to supply an olefin-containing stream to the plurality of alkylation zones, thereby producing an alkylate stream. The multi-zone alkylation reactor further includes a first alkylate product conduit to transport the alkylate stream from the first mechanically separated catalytic volume to the second mechanically separated catalytic volume.

An embodiment of an alkylation system includes a multi-zone alkylation reactor with a recirculation pump. The multi-zone alkylation reactor includes a plurality of alkylation zones spaced vertically in a series configuration and a vertical partition splitting the plurality of alkylation zones into two mechanically separated catalytic volumes, along with a plurality of olefinic feed inlets positioned to supply an olefin-containing stream to each of the plurality of alkylation zones in the two mechanically separated catalytic volumes, an isobutane inlet to supply isobutane to a first alkylation zone in a first mechanically separated catalytic volume, a first plurality of conduits configured for fluid flow of the alkylate stream through the plurality of alkylation zones in the first mechanically separated catalytic volume, a first alkylate product conduit to transport the alkylate stream from a last alkylation zone in the first mechanically separated catalytic volume to the first alkylation zone in a second mechanically separated catalytic volume, a second plurality of conduits configured for fluid flow of the alkylate stream through the plurality of alkylation zones in the second mechanically separated catalytic volume, and a second alkylate product conduit to transport the alkylate stream from a last alkylation zone in the second mechanically separated catalytic volume to a recirculation pump. The fluid flows may be downward or upward through the plurality of alkylation zones. The olefin-containing stream contains olefins, such as ethylene and propylene, and light components, such as hydrogen and methane. The alkylate stream contains alkylates produced by reaction of olefins in the olefin-containing stream with the isobutane. Alkylates include a mixture of high-octane, branched-chain paraffinic hydrocarbons. Each of the mechanically separated catalytic volumes may be configured as a hydraulically sealed reaction chamber. Each of the plurality of alkylation zones contains a solid acid alkylation catalyst. The recirculation pump is configured for receiving the alkylate stream from the second alkylate product conduit, directing a first portion of the alkylate stream for further processing to produce an enriched alkylate product containing high-octane, branched-chain paraffinic hydrocarbons, and recirculating a second portion of the alkylate stream to the first mechanically separated catalytic volume, thereby maintaining a desired ratio of isobutane to olefins. In certain embodiments, this ratio ranges from about 300:1 to about 500:1. The flowrate of the recirculation pump may decrease by at least 50 percent compared to a traditional alkylation reactor recirculation pump.

Another embodiment of an alkylation system to increase alkylate products includes a multi-zone alkylation reactor and a recirculation pump. Certain embodiments include a deisobutanizer in fluid communication with the recirculation pump. For example, the multi-zone alkylation reactor includes a plurality of alkylation zones spaced vertically in a series configuration and at least one vertical partition splitting the plurality of alkylation zones into at least two mechanically separated catalytic volumes, a plurality of olefinic feed inlets positioned to supply an olefin-containing stream to each of the plurality of alkylation zones in the at least two mechanically separated catalytic volumes, an isobutane inlet to supply isobutane to a first alkylation zone in a first mechanically separated catalytic volume, a first plurality of conduits configured for fluid flow of the alkylate stream through the plurality of alkylation zones in the first mechanically separated catalytic volume, a first alkylate product conduit to transport the alkylate stream from a last alkylation zone in the first mechanically separated catalytic volume to the first alkylation zone in a second mechanically separated catalytic volume, a second plurality of conduits configured for fluid flow of the alkylate stream through the plurality of alkylation zones in the second mechanically separated catalytic volume, and a second alkylate product conduit to transport the alkylate stream from a last alkylation zone in the second mechanically separated catalytic volume to a recirculation pump. The alkylate stream contains alkylates produced by reaction of olefins in the olefin-containing stream with the isobutane. The fluid flows may be downward or upward through the plurality of alkylation zones. The recirculation pump is configured for receiving the alkylate stream from the second alkylate product conduit, directing a first portion of the alkylate stream to a deisobutanizer, and recirculating a second portion of the alkylate stream to the first mechanically separated catalytic volume, thereby maintaining a desired molar ratio of isobutane to olefins. In certain embodiments, this ratio ranges from about 300:1 to about 500:1. The deisobutanizer is configured for receiving a first portion of the alkylate stream from the recirculation pump and separating the first portion of the alkylate stream into (i) a recycle isobutane stream to supply to the first mechanically separated catalytic volume; (ii) a normal butane stream; and (iii) a product stream containing a mixture of high-octane, branched-chain paraffinic hydrocarbons.

Embodiments include methods for production of an alkylate involving a multi-zone alkylation reactor. For example, this multi-zone alkylation reactor may include two mechanically separated catalytic volumes with a first and a second plurality of alkylation zones loaded with alkylation catalysts, a first plurality of conduits configured for downward or upward fluid flow through the first plurality of alkylation zones in a first mechanically separated catalytic volume, and a second plurality of conduits configured for downward or upward fluid flow through the second plurality of alkylation zones in a second mechanically separated catalytic volume. One such method includes the steps of (i) supplying an isobutane stream through an isobutane inlet to the multi-zone alkylation reactor, (ii) supplying an olefin-containing stream through a first plurality of olefinic feed inlets positioned at each of the first plurality of alkylation zones in the first mechanically separated catalytic volumes and through a second plurality of olefinic feed inlets positioned at the second plurality of alkylation zones in the second mechanically separated catalytic volumes, (iii) directing an alkylate stream containing alkylates produced by reaction of the olefin-containing stream with the isobutane in each of the first plurality of alkylation zones through a first plurality of conduits configured for downward fluid flow of the alkylate stream through the first plurality of alkylation zones in the first mechanically separated catalytic volume, (iv) directing the alkylate stream from a last alkylation zone in the first mechanically separated catalytic volume through a first alkylate product conduit to the first alkylation zone in a second mechanically separated catalytic volume, (v) directing the alkylate stream from the first alkylation zone in the second mechanically separated catalytic volume through a second plurality of conduits configured for downward fluid flow of the alkylate stream through the second plurality of alkylation zones in the second mechanically separated catalytic volume, and (vi) directing the alkylate stream from a last alkylation zone in the second mechanically separated catalytic volume through a second alkylate product conduit to a recirculation pump. In certain embodiments, the method can include the steps of directing a first portion of the alkylate stream from the recirculation pump for further processing to produce an enriched alkylate product containing high-octane, branched-chain paraffinic hydrocarbons, and recirculating a second portion of the alkylate stream to the first mechanically separated catalytic volume, thereby a desired ratio of isobutane to olefins. In certain embodiments, this ratio ranges from about 300:1 to about 500:1.

Embodiments include methods for regenerating an alkylation zone of a multi-zone alkylation reactor. The multi-zone alkylation reactor includes two mechanically separated catalytic volumes with a first and a second plurality of alkylation zones loaded with spent alkylation catalysts, a first plurality of conduits configured for downward or upward fluid flow through the first plurality of alkylation zones in a first mechanically separated catalytic volume, and a second plurality of conduits configured for upward or downward fluid flow through the second plurality of alkylation zones in a second mechanically separated catalytic volume. One such method includes the steps of: (i) directing a regeneration stream to a compressor to produce a compressed regeneration stream, (ii) supplying the compressed regeneration stream to a heat exchanger positioned to cross-flow the compressed regeneration stream with a spent regeneration stream from an outlet from a multi-zone alkylation reactor to produce a hot compressed regeneration stream and a cooled spent regeneration stream, (iii) directing the hot compressed regeneration stream from the heat exchanger to a heater thereby to produce a regeneration feed stream, (iv) supplying the regeneration feed stream to an inlet of the multi-zone alkylation reactor, (v) directing the regeneration feed stream, through the first plurality of alkylation zones and the first plurality of conduits in the first mechanically separated catalytic volume and through the second plurality of alkylation zones and the second plurality of conduits in the second mechanically separated catalytic volume, to facilitate interaction with the spent alkylation catalyst in the first and second plurality of alkylation zones under catalyst regeneration conditions to regenerate the spent alkylation catalyst and to produce a regenerated catalyst having substantially increased alkylation activity and a spent regeneration stream exiting at an outlet of the multi-zone alkylation reactor. In certain embodiments, the method can further include the step of supplying the spent regeneration stream from the outlet of the multi-zone alkylation reactor to the heat exchanger, and directing the spent regeneration stream from the heat exchanger to a vapor-liquid separator to separate spent material of the cooled spent regeneration stream to produce the regeneration stream and a spent material stream containing soluble and insoluble coke. In certain embodiments, the regeneration stream contains hydrogen-rich gas. The hydrogen-rich gas may contain about 70 to 90 weight percent (wt. %) of hydrogen. In certain embodiments, the heater is a fired heater.

BRIEF DESCRIPTION OF DRAWINGS

These embodiments and other features, aspects, and advantages of the disclosure will be better understood in conjunction with the following descriptions, claims, and accompanying drawings. It is to be noted, however, that the drawings illustrate only certain embodiments of the disclosure and, therefore, are not to be considered limiting of the scope of the disclosure.

DETAILED DESCRIPTION

Figure 1:
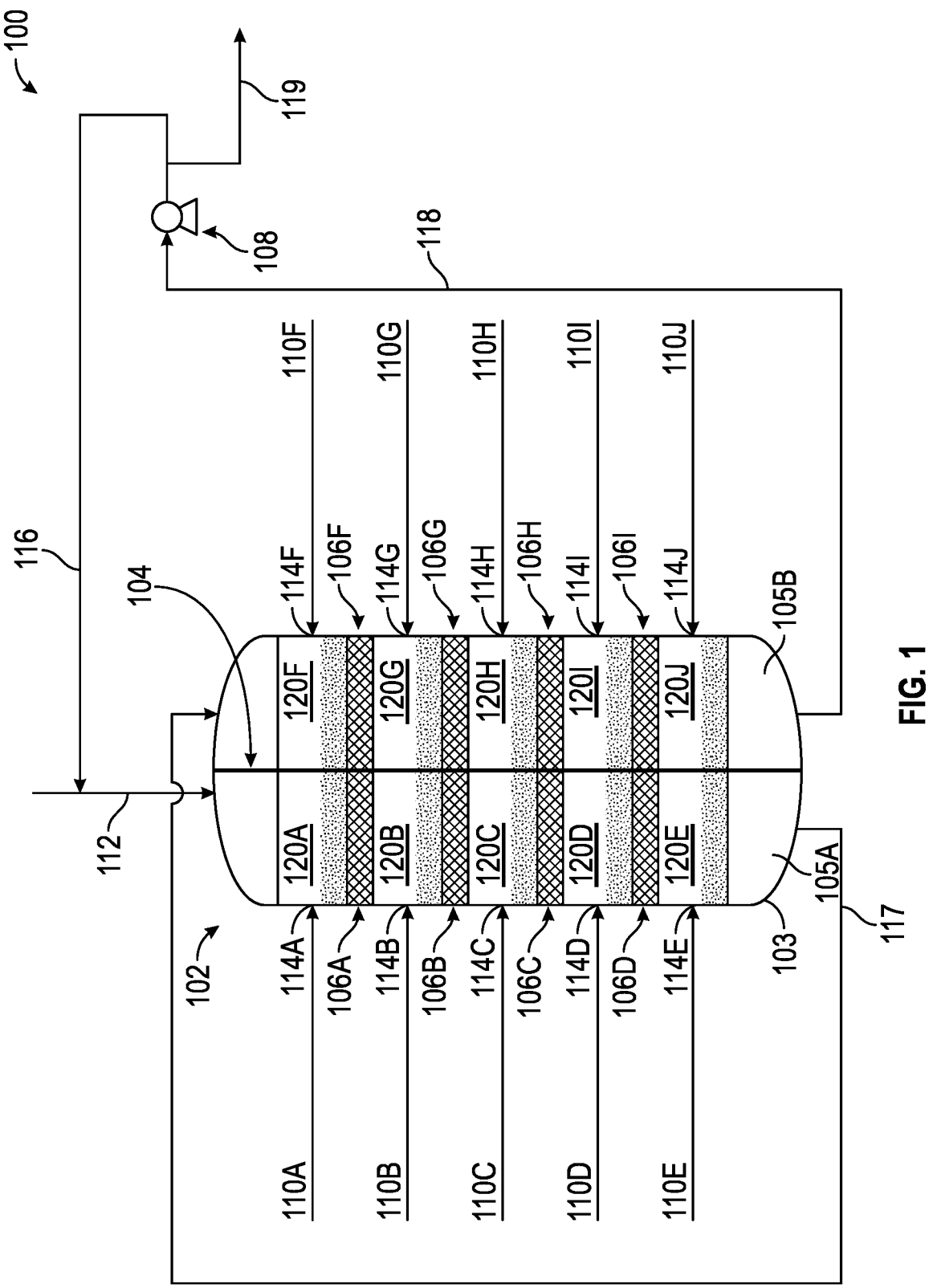
FIG. 1 is an illustrative diagram of a multi-zone alkylation system, according to an embodiment of the disclosure.

The present disclosure provides for multi-zone alkylation systems and methods for alkylate production using these systems. So that the manner in which the features and advantages of the embodiments of the methods and systems disclosed herein, as well as others that will become apparent, may be understood in more detail, a more particular description of non-limiting embodiments of methods and systems is provided. In the following description, numerous details are set forth in order to provide a thorough understanding of the various embodiments. In other instances, well-known processes, devices, and systems may not been described in particular detail in order not to unnecessarily obscure the various embodiments. Additionally, illustrations of the various embodiments may omit certain features or details in order to not obscure the various embodiments.

Alkylation reactors can be utilized to facilitate processing light olefins into high-quality, low Reid vapor pressure (RVP) alkylate. An embodiment of an alkylation system includes a multi-zone alkylation reactor. This multi-zone alkylation reactor includes a plurality of alkylation zones spaced vertically in a series configuration. The multi-zone alkylation reactor includes at least one partition splitting the plurality of alkylation zones into at least a first mechanically separated catalytic volume and a second mechanically separated catalytic volume. In certain embodiments, the partition may be a vertical partition or a horizontal partition. The multi-zone alkylation reactor also includes an isobutane inlet positioned to supply an isobutane stream to the first mechanically separated catalytic volume and at least one olefinic feed inlet positioned to supply an olefin-containing stream to the plurality of alkylation zones. The isobutane and the olefin feed react under catalytic alkylation conditions to produce an alkylate stream. The multi-zone alkylation reactor further includes a first alkylate product conduit to transport the alkylate stream from the first mechanically separated catalytic volume to the second mechanically separated catalytic volume. The alkylate stream contains alkylate products along with unreacted isobutane and olefins. The alkylate stream may continue in a first fluid flow direction until it reaches a last alkylation zone in the first mechanically separated catalytic volume. The alkylate stream may then be directed via a first alkylate product conduit from the last alkylation zone in the first mechanically separated catalytic volume to a first alkylation zone in the second mechanically separated catalytic volume. This alkylate stream may be directed in a second fluid flow direction to a last alkylation zone in the second mechanically separated catalytic volume. In certain embodiments, the first fluid flow direction and the second fluid flow direction are both a downward direction. In certain embodiments, the first fluid flow direction is a downward direction and the second fluid flow direction is an upward direction. In certain embodiments, the first fluid flow direction is an upward direction and the second fluid flow direction is a downward direction. In certain embodiments, the first fluid flow direction and the second fluid flow direction are both an upward direction. In certain embodiments, the first fluid flow direction and the second fluid flow direction may include a leftward flow, a rightward flow, or a combination thereof in corresponding mechanically separated catalytic volumes. In certain embodiments, two or more partitions positioned vertically or horizontally may be positioned to split the plurality of alkylation zones into at least two or more mechanically separated catalytic volumes.

An embodiment of an alkylation system includes a multi-zone alkylation reactor. The multi-zone alkylation reactor may include a plurality of alkylation zones spaced vertically in a series configuration, as well as at least one vertical partition splitting the plurality of alkylation zones into at least two mechanically separated catalytic volumes. The multi-zone alkylation reactor may include a plurality of olefinic feed inlets positioned to supply an olefin-containing stream to each of the plurality of alkylation zones in the at least two mechanically separated catalytic volumes. The multi-zone alkylation reactor may also include an isobutane inlet to supply isobutane to a first alkylation zone in a first mechanically separated catalytic volume. The multi-zone alkylation reactor may further include a first plurality of conduits configured for fluid flow of the alkylate stream through the plurality of alkylation zones in the first mechanically separated catalytic volume. In certain embodiments, a first alkylate product conduit of the multi-zone alkylation reactor may transport the alkylate stream from a last alkylation zone in the first mechanically separated catalytic volume to a first alkylation zone in a second mechanically separated catalytic volume. The multi-zone alkylation reactor may include a second plurality of conduits configured for fluid flow of the alkylate stream through the plurality of alkylation zones in the second mechanically separated catalytic volume. The fluid flows may be downward or upward through the plurality of alkylation zones. Additionally, a second alkylate product conduit of the multi-zone alkylation reactor may transport the alkylate stream out of a last alkylation zone in the second mechanically separated catalytic volume. In certain embodiments, the alkylate stream is then directed to a recirculation pump. In embodiments having more than one vertical partition, a third alkylate product conduit may transport the alkylate stream from the last alkylation zone in the second mechanically separated catalytic zone to a first alkylation zone in a third mechanically separated catalytic volume. Embodiments of the multi-zone alkylation reactor may be configured to include three catalytic volumes separated by two vertical partitions, four catalytic volumes separated by three vertical partitions, and so forth. Moreover, although sometimes described with reference to downward fluid flow of the alkylation stream through alkylation zones, the multi-zone alkylation reactor may be designed for upward fluid flow in all or a portion of the mechanically separated catalytic zones.

The olefin-containing stream may contain olefins, such as ethylene and propylene, and light components, such as hydrogen and methane. The alkylate stream may contain alkylates produced by reaction of olefins in the olefin-containing stream with the isobutane. Alkylates include a mixture of high-octane, branched-chain paraffinic hydrocarbons. As referred to herein, a high-octane hydrocarbon has an octane rating equal to or greater than a predetermined threshold, such as 90. For example, high-octane hydrocarbons may include branched-chain isomers of octane, such as 2,2,4-trimethylpentane (iso-octane) and 2,2,3-trimethyl pentane, and other trimethyl isomers of C8+ hydrocarbons. Each of the mechanically separated catalytic volumes may be configured as a hydraulically sealed reaction chamber. Each of the plurality of alkylation zones may contain a solid acid alkylation catalyst.

The recirculation pump of certain embodiments may be configured for receiving the alkylate stream from the second alkylate product conduit and directing a portion of the alkylate stream for further processing to produce an enriched alkylate product containing high-octane paraffinic hydrocarbons. In certain embodiments, the recirculation pump may be configured for recirculating a second portion of the alkylate stream to the first mechanically separated catalytic volume. As such, the recirculation pump may maintain a desired ratio of isobutane to olefins in the multi-zone alkylation reactor. In certain embodiments, this ratio may range from about 300:1 to about 500:1, or from about 350:1 to about 500:1, or from about 400:1 to about 500:1, or from about 300:1 to about 450:1, or from about 300:1 to about 400:1. The flowrate of the recirculation pump may decrease by at least 50 percent compared to a traditional alkylation reactor recirculation pump, in certain embodiments. The flowrate of the recirculation pump may decrease by at least 30 percent or 40 percent compared to a traditional alkylation reactor recirculation pump, in certain embodiments. The flowrate of the recirculation pump may decrease by at least 60 percent compared to a traditional alkylation reactor recirculation pump, in certain embodiments. The decreased recirculation flowrate of certain embodiments may correspond to decreased operating costs, without compromising product yield, in certain embodiments.

FIG. 1 is an illustrative diagram of a multi-zone alkylation reactor, according to an embodiment of the disclosure. In certain embodiments, an alkylation system 100 contains a multi-zone alkylation reactor 102. The multi-zone alkylation reactor 102 includes a shell 103 or enclosure. The multi-zone alkylation reactor 102 contains a plurality of alkylation zones 120, such as alkylation zones 120A, 120B, 120C, 120D, 120E, 120F, 120G, 120H, 120I, and 120J, defined within the shell 103. Alkylation zones 120A, 120B, 120C, 120D, and 120E are spaced vertically in a series configuration. Alkylation zones 120F, 120G, 120H, 120I, and 120J are spaced vertically in a series configuration. At least one vertical partition 104 separates the plurality of alkylation zones 120 into at least two mechanically separated catalytic volumes 105. In the illustrated embodiment, alkylation zones 120A, 120B, 120C, 120D, and 120E are defined within a first mechanically separated catalytic volume 105A, and alkylation zones 120F, 120G, 120H, 120I, and 120J are defined within a second mechanically separated catalytic volume 105B. The vertical partition 104 may be a solid plate that extends vertically within the shell 103. In certain embodiments, this plate may be made of a metal or an inert material. For example, the vertical partition of certain embodiments extends in a plane defined from an upper inner surface to a lower inner surface of the shell 103 and extends from a first lateral inner surface to an opposite, second lateral inner surface of the shell 103. The vertical partition 104 may be welded or irremovably coupled to a suitable portion of the shell 103 of the multi-zone alkylation reactor 102, in certain embodiments. In other embodiments, vertical partition 104 may be removable and attached to the shell 103 with partition support attachments. Although illustrated with a single vertical partition 104, two or more vertical partitions 104 may be implemented in the multi-zone alkylation reactor 102, based on a variety of operational factors, such as physical space availability, ease of accessibility of internal elements, and/or a target product quality. Moreover, although illustrated with 10 alkylation zones 120, the multi-zone alkylation reactor 102 may be designed to include any suitable number of alkylation zones 120, such as 2, 4, 6, 8, 12, 14, or more. The vertical partitions 104 of the present disclosure effectively increase a number of traditional alkylation stages by a number of vertical partitions 104 to increase the number of alkylation zones 120.

A plurality of olefinic feed inlets 114, such as olefinic feed inlets 114A, 114B, 114C, 114D, 114E, 114F, 114G, 114H, 114I, and 114J, are positioned to supply olefin-containing streams 110 through the shell 103 and to each of the plurality of alkylation zones 120 respectively inside the two mechanically separated catalytic volumes 105. For example, each of olefin-containing streams 110A, 110B, 110C, 110D, 110E, 110F, 110G, 110H, 110I, and 110J may be received by a corresponding one of the alkylation zones 120A, 120B, 120C, 120D, 120E, 120F, 120G, 120H, 120I, and 120J, through corresponding olefinic feed inlets 114A, 114B, 114C, 114D, 114E, 114F, 114G, 114H, 114I, and 114J, respectively. The olefin-containing streams 110 of certain embodiments contain olefins, such as ethylene and propylene, and light components, such as hydrogen and methane. In the illustrated embodiment, an isobutane stream 112 is provided through an inlet defined in the shell 103 and supplied to the first alkylation zone 120A in the first mechanically separated catalytic volume 105A. In certain embodiments, a portion of isobutane is also premixed with an olefinic feed stream 110 that is provided to the olefinic feed inlets 114. Each of the mechanically separated reaction volumes 105A and 105B may be configured as a hydraulically sealed reaction chamber. The two mechanically separated catalytic volumes 105 having the alkylation zones 120 spaced vertically in a series configuration may increase the total fluid flow length of the multi-zone alkylation reactor 102 available for the alkylation reaction, for a given nominal length of the shell 103. Moreover, the mechanically separated catalytic volumes 105 may also increase a number of the plurality of olefinic feed inlets 114 of the multi-zone alkylation reactor 102, compared to a previously implemented reactor. In certain embodiments, this multi-zone alkylation reactor 102 configuration allows for maintaining the rate of the primary reaction of olefin with isoparaffin at least two orders of magnitudes higher than the rate of the secondary reactions among the olefins. In certain embodiments, this configuration of the multi-zone alkylation reactor 102 allows for maintaining optimal I/O ratios. Each alkylation zone 120 contains an alkylation catalyst suitable for producing alkylates, as discussed below. The reactor conditions may generally be similar to reactor conditions of previously implemented alkylation reactors, such as K-SAAT reactors, in certain embodiments. In some embodiments, the alkylation reactions are performed at pressures ranging between 200 and 300 psi(g) and at temperatures ranging between 43 and 82° C.

According to some embodiments, each of the plurality of alkylation zones 120 contains a solid acid alkylation catalyst, for example, a K-SAAT™ catalyst (KBR, Houston, Tex.). Aspects of solid acid catalyst alkylation are described in U.S. Pat. Nos. 9,079,815 and 10,179,753, and U.S. Patent Publication No. 2020/0031733, for example, which are hereby incorporated by reference. The alkylation reaction between isobutane and olefins, such as those contained in the olefin-containing streams 110, may take place over a solid acid catalyst on fixed beds in the alkylation zones 120. Indeed, each alkylation zone 120 of the present embodiment is illustrated as having a respective fixed bed therein. The solid acid catalyst may be a zeolite catalyst, as described in the referenced patents and may comprise metals, such as platinum, palladium, and/or nickel.

In the present embodiment, the multi-zone alkylation reactor 102 includes a plurality of conduits 106 (e.g., flow channels, distributor plates) to direct the fluid flow of reactants and the products as part of the alkylate stream through at least a portion of the plurality of alkylation zones 120. In certain embodiments, the conduits 106 interconnect the alkylation zones 120 within the respective mechanically separated catalytic volume 105. For example, within the first mechanically separated catalytic volume 105A, the alkylate stream within alkylation zone 120A may flow sequentially through conduit 106A, alkylation zone 120B, conduit 106B, alkylation zone 120C, conduit 106C, alkylation zone 120D, conduit 106D, and alkylation zone 120E. The isobutane in the alkylate stream within each of these alkylation zones 120 may react with the olefins in a respective one of the olefin-containing streams 110, as discussed above. The alkylate stream contains alkylates produced by reaction of olefins in the olefin-containing stream with the isobutane from the isobutane stream 112, in addition to the unreacted olefins and isobutane. Alkylates include a mixture of high-octane, branched-chain paraffinic hydrocarbons. As used herein, a high-octane refers to a hydrocarbon or mixture thereof having an octane rating that is equal to or greater than a predetermined threshold. For example, high-octane hydrocarbons of certain embodiments have an octane rating of 90 of more. Achieving the valuable high-octane fuels includes a primary reaction between isobutane and butene to produce isooctane. As stated herein, the alkylation system 100 produces alkylates that have low RVP, which in turn, increases the alkylate yield. In the multi-zone alkylation reactor 102, isobutane and butene are alkylated to produce isooctane and n-butane. A subsequent fractionation process may crack the alkylate stream via two reactions. In a first reaction, isooctane can be cracked into iso-pentane and propylene. In a second reaction, the isobutane and the propylene can be cracked into iso-heptane.

In the illustrated embodiment, a first alkylate product conduit 117 is positioned to transport the alkylate stream from a last alkylation zone 120E (or bottommost alkylation zone) in the first mechanically separated catalytic volume 105A to the first alkylation zone 120F (or topmost alkylation zone) in the second mechanically separated catalytic volume 105B. The plurality of conduits 106 direct fluid flow of the alkylate stream through the alkylation zones 120 in the second mechanically separated catalytic volume 105B. For example, the alkylate stream within alkylation zone 120F may flow sequentially through conduit 106F, alkylation zone 120G, conduit 106G, alkylation zone 120H, conduit 106H, alkylation zone 120I, conduit 106I, and alkylation zone 120J. The isobutane in the alkylate stream within each of these alkylation zones 120 may react with olefins in a respective one of the olefin-containing streams 110, as discussed above.

In certain embodiments, a second alkylate product conduit 118 may transport the alkylate stream from the last alkylation zone 120J (or bottommost alkylation zone) in the second mechanically separated catalytic volume 105B to a recirculation pump 108 of the alkylation system 100. The recirculation pump 108 may be any suitable fluid moving device for receiving the alkylate stream from the second alkylate product conduit 118. The alkylation system 100 may therefore produce a first portion 119 of the alkylate stream as a product or intermediate product and recirculate a second portion 116 of the alkylate stream back to the first mechanically separated catalytic volume 105A to maintain a desired or target ratio of isobutane to olefins therein. In certain embodiments, the target ratio of isobutane to olefins ranges from about 300:1 to about 500:1. In certain embodiments, the target ratio of isobutane to olefins is about 400:1. As used herein, a threshold or high ratio of isobutane to olefins refers to a ratio of about 300:1 or higher.

In certain embodiments, the amount of alkylate recycled to the multi-zone alkylation reactor 102 is calculated to minimize macro-mixing properties and micro-mixing properties. The presently disclosed alkylation system 100 having the one or more vertical partitions 104 provides a significant reduction of 50% or more in the amount of alkylate stream recirculated back to the multi-zone alkylation reactor 102, compared to systems that do not implement vertical partitions.

Moreover, the addition of the vertical partition 104 can reduce the cross-sectional area of each alkylation zones 120, compared to an alkylation reactor without a partition. In the present embodiments, the length (e.g., reaction length, zone height) of the alkylation zones 120 may remain the same. Each mechanically separated catalytic volume 105 can have a balanced distribution of the respective olefin-containing stream 110 and isobutane stream 112 across the alkylation zones 120. Although illustrated as including downward flow of fluid through each of the mechanically separated catalytic volumes 105, other embodiments of the present disclosure may alternatively provide upward flow of fluid through one, more than one, or all mechanically separated catalytic volumes 105. As used herein, a downward flow direction may generally refer to a flow direction corresponding to or parallel with a force of gravity, and an upward flow direction may generally refer to a flow direction that is opposite the force of gravity. Moreover, certain embodiments of the present disclosure may include designs of the multi-zone alkylation reactor 102 in which the shell 103 is generally horizontally extending, instead of generally vertically extending as illustrated in FIG. 1. In such embodiments, the vertical partition 104 may be adjusted to be a horizontal partition that facilitates leftward flow, rightward flow, or a combination thereof in corresponding mechanically separated catalytic volumes 105.

In certain embodiments, the solid acid alkylation catalyst of the alkylation zones 120 may contain zeolite material supporting non-precious metals. An example of a suitable catalyst is KBR's ExSact™ catalyst, which is a zeolite-based catalyst that is selective to high-octane TMPs and eliminates acid-soluble oils. Suitable catalysts may have an improved mass transfer to prevent pore blockage, may promote alkylation over polymerization reactions, and may be highly selective to 2,3,3- and 2,3,4-trimethylpentane, with minimal isomerization of trimethylpentanes to dimethylhexanes. In some embodiments, the alkylation reactions within the multi-zone alkylation reactor 102 are performed at low temperatures (e.g., 40-80° C.), are slightly exothermic, and provide a radial temperature profile or distribution within about 2.8 or 3° C. In the present embodiments, the mechanically separated catalytic volumes 105 can reduce macro-mixing properties and micro-mixing properties within the multi-zone alkylation reactor 102. Reduced macro-mixing properties and micro-mixing properties include minimizing the mixing volume in the multi-zone alkylation reactor 102 and reducing the back-up mixing supplied to the multi-zone alkylation reactor 102, with the reduction of the portion 116 of the alkylate stream recycled back to the multi-zone alkylation reactor 102 by the recirculation pump 108.

The ratio of isobutane to olefins may generally control the alkylate concentration within the multi-zone alkylation reactor 102. At the target or high ratio of isobutane to olefins that is 300:1 or higher, the multi-zone alkylation reactor 102 can produce high octane alkylate. In addition, the high ratio of isobutane to olefins may improve the lifespan of the catalyst. In the embodiments, the flowrate of the alkylation reactor recirculation pump 108 can decrease by at least 50 percent compared to a recirculation pump in a traditional alkylation system. The decreased flowrate of the recirculation pump 108 can increase the amount of the alkylate stream that can be further processed.

Embodiments also include methods for increasing alkylate production and reducing recirculation flow to a multi-zone alkylation reactor. One such method for reducing recirculation to the multi-zone alkylation reactor may involve directing an isobutane stream to a plurality of alkylation zones in the multi-zone alkylation reactor. The multi-zone alkylation reactor may contain at least one vertical partition that separates the plurality of alkylation zones into at least two mechanically separated catalytic volumes. An olefin-containing stream may be directed via a plurality of olefinic feed inlets to each alkylation zone in two or more mechanically separated catalytic volumes. Isobutane may be supplied to the first alkylation zone in a first mechanically separated catalytic volume through an isobutane inlet. In an embodiment, the isobutane may react with olefins at the first alkylation zone in the first mechanically separated catalytic volume to produce an alkylate stream. As such, an amount of alkylates in the alkylate stream may increase as the isobutane and each olefin-containing streams react in respective alkylation zones, continuing through until the last alkylation zone in the first mechanically separated catalytic volume. The alkylate stream may then be directed via a first alkylate product conduit from the last alkylation zone in the first mechanically separated catalytic volume to a first alkylation zone in a second mechanically separated catalytic volume. The alkylate stream can be directed from the first alkylation zone in the second mechanically separated catalytic volume to continue the alkylation reaction between the isobutane and each olefin-containing stream provided to the alkylation zones in the second mechanically separated catalytic volume. This alkylate stream can be directed to a last alkylation zone in the second mechanically separated catalytic volume, increasing the amount of alkylates therein. The alkylate stream may then be directed from the last alkylation zone in the second mechanically separated catalytic volume to a recirculation pump. The alkylate stream exiting the recirculation pump may be separated into a first portion and a second portion. The first portion of the alkylate stream may be directed from the recirculation pump to be further processed to produce an enriched alkylate product containing high-octane, branched-chain paraffinic hydrocarbons. The second portion of the alkylate stream may be directed from the recirculation pump to the first alkylation zone in the first mechanically separated catalytic volume to maintain a desired ratio of isobutane to olefins. In certain embodiments, this ratio ranges from about 300:1 to about 500:1.

Figure 2:
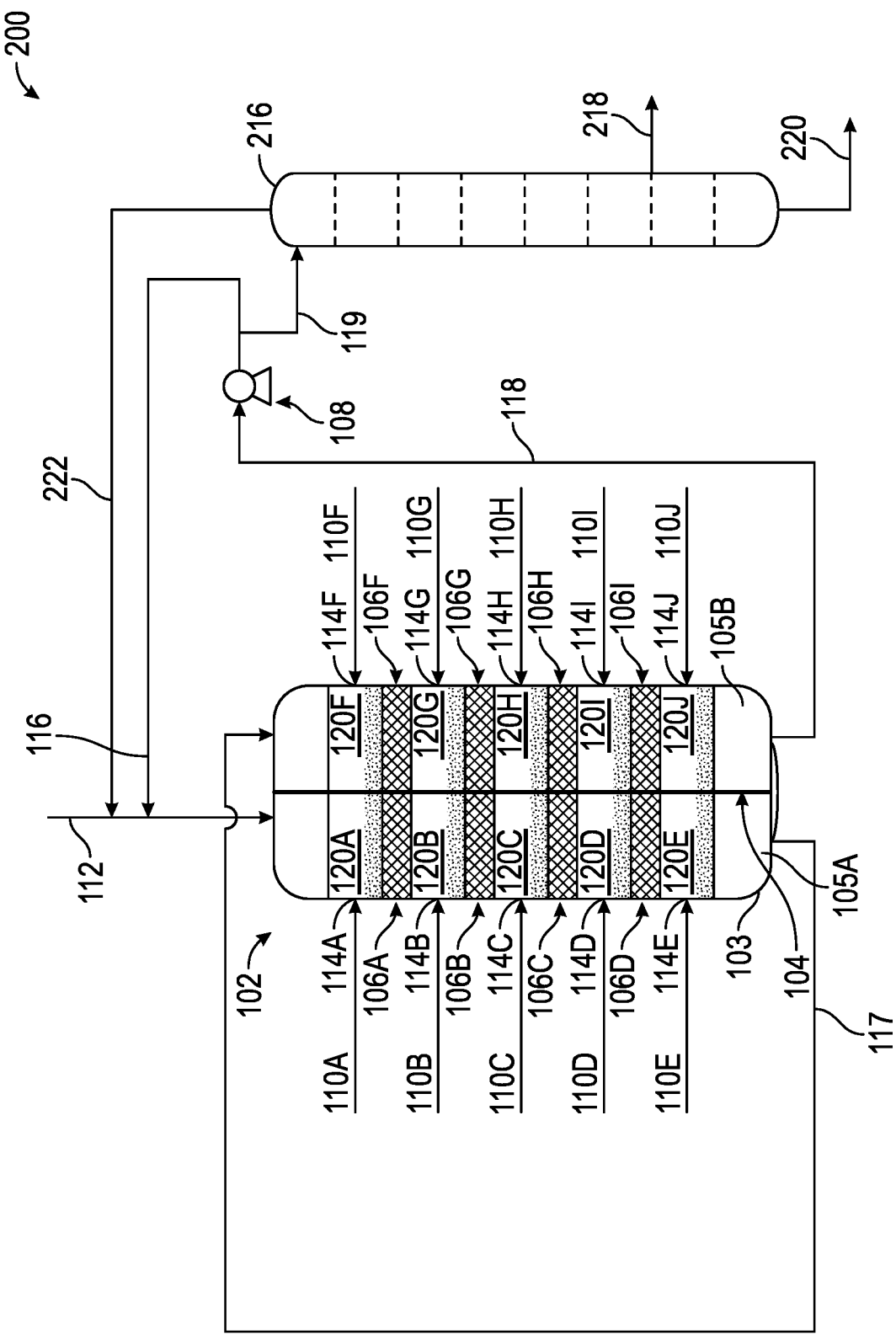
FIG. 2 is an illustrative diagram of a multi-zone alkylation system with a deisobutanizer, according to an embodiment of the disclosure.

FIG. 2 is an illustrative diagram of a multi-zone alkylation system 200 with a deisobutanizer 216, according to an embodiment of the disclosure. In certain embodiments, the alkylate production system 200 contains a multi-zone alkylation reactor 102. The multi-zone alkylation reactor 102 of FIG. 2 may generally correspond to the multi-zone alkylation reactor 102 of FIG. 1, where corresponding elements may be described with reference to their operation within the alkylate production system 200. For example, the multi-zone alkylation reactor 102 of the present embodiment contains a plurality of alkylation zones 120, such as alkylation zones 120A, 120B, 120C, 120D, 120E, 120F, 120G, 120H, 120I, and 120J, which may be defined within a shell 103 and spaced vertically in a series configuration. At least one vertical partition 104 separates the plurality of alkylation zones 120 into at least two mechanically separated catalytic volumes 105A and 105B. A plurality of olefinic feed inlets 114, such as olefinic feed inlets 114A, 114B, 114C, 114D, 114E, 114F, 114G, 114H, 114I, and 114J may be positioned to supply an olefin-containing stream 110 to each of the plurality of alkylation zones 120 in the two mechanically separated catalytic volumes 105A and 105B. An isobutane stream 112 is provided to a first alkylation zone 120A in a first mechanically separated catalytic volume 105A. In the present embodiment, the multi-zone alkylation reactor 102 includes a plurality of conduits 106 to direct fluid flow of the alkylate stream through at least a portion of the plurality of alkylation zones 120. For example, the alkylate stream within alkylation zone 120A may flow sequentially through conduit 106A, alkylation zone 120B, conduit 106B, alkylation zone 120C, conduit 106C, alkylation zone 120D, conduit 106D, and alkylation zone 120E. The first plurality of conduits 106A, 106B, 106C, and 106D may be configured to provide downward fluid flow of the alkylate stream from alkylation zone 120A through alkylation zones 120B, 120C, 120D, and 120E in the first mechanically separated catalytic volume 105A.

A first alkylate product conduit 117 may transport the alkylate stream from a last alkylation zone 120E in the first mechanically separated catalytic volume 105A to a first alkylation zone 120F in a second mechanically separated catalytic volume 105B. A second plurality of conduits 106F, 106G, and 106H, and 106I may be configured to provide downward fluid flow of the alkylate stream from alkylation zone 120F through alkylation zones 120G, 120H, 120I, and 120J in the second mechanically separated catalytic volume 105B. For example, the alkylate stream within alkylation zone 120F may flow sequentially through conduit 106F, alkylation zone 120G, conduit 106G, alkylation zone 120H, conduit 106H, alkylation zone 120I, conduit 106I, and alkylation zone 120J. A second alkylate product conduit 118 may transport the alkylate stream from a last alkylation zone 120J in the second mechanically separated catalytic volume 105B to a recirculation pump 108. The recirculation pump 108 of the alkylation production system 200 is configured for receiving the alkylate stream from the second alkylate product conduit 118 and recirculating a first portion 119 of the alkylate stream from the recirculation pump 108 to a deisobutanizer 216. The alkylation production system 200 may also recirculate a second portion 116 of the alkylate stream back to the first mechanically separated catalytic volume 105A directly to maintain a desired or target ratio of isobutane to olefins. In certain embodiments, the target ratio of isobutane to olefins ranges from about 300:1 to about 500:1. In certain embodiments, the target ratio of isobutane to olefins is about 400:1. As used herein, a threshold or high ratio of isobutane to olefins refers to a ratio of about 300:1 or higher.

The deisobutanizer 216 of the alkylate production system 200 is configured for receiving the first portion 119 of the alkylate stream from the recirculation pump 108 and separating the first portion 119 of the alkylate stream into (i) a recycle isobutane stream 222 to supply to the first mechanically separated catalytic volume 105A, (ii) a normal butane or n-butane stream 218, and (iii) a product stream 220 containing a mixture of high-octane, branched-chain paraffinic hydrocarbons. As used herein, a high-octane component refers to a hydrocarbon or mixture thereof having an octane rating that is equal to or greater than a predetermined threshold, such as an octane rating of 90 of more. The recycle isobutane stream 222 may be rich in isobutane and may be taken as a side draw to recycle to the multi-zone alkylation reactor 102 for further alkylate production. As presently recognized, the alkylation production system 200 having the one or more vertical partitions 104 provides a significant reduction of 50% or more in the amount of alkylates recirculated back to the multi-zone alkylation reactor 102, compared to systems that do not implement vertical partitions.

Another embodiment of methods for increasing alkylate production and reducing recirculation flow to a multi-zone alkylation reactor involves inclusion of a deisobutanizer in the alkylation system. An olefin-containing stream may be directed via a plurality of olefinic feed inlets to each alkylation zone in two or more mechanically separated catalytic volumes of the multi-zone alkylation reactor. Isobutane may be supplied via an isobutane inlet. The isobutane may interact with the olefin-containing stream starting at a first alkylation zone in a first mechanically separated catalytic volume to produce the alkylate stream. As such, the alkylate stream can continue to include the alkylates produced by the reaction of the isobutane and olefins from each of the olefin-containing streams in each alkylation zones. The alkylate stream may continue in a first fluid flow direction until it reaches a last alkylation zone in the first mechanically separated catalytic volume. The alkylate stream may then be directed via a first alkylate product conduit from the last alkylation zone in the first mechanically separated catalytic volume to a first alkylation zone in the second mechanically separated catalytic volume. The alkylate stream can include the alkylates produced by the reaction of the isobutane and olefins from each of the olefin-containing streams in each alkylation zone. This alkylate stream may be directed in a second fluid flow direction to a last alkylation zone in the second mechanically separated catalytic volume. In certain embodiments, the first fluid flow direction and the second fluid flow direction are both a downward direction. In certain embodiments, the first fluid flow direction is a downward direction and the second fluid flow direction is an upward direction. In certain embodiments, the first fluid flow direction is an upward direction and the second fluid flow direction is a downward direction. In certain embodiments, the first fluid flow direction and the second fluid flow direction are both an upward direction. The alkylate stream may then be directed from the last alkylation zone in the second mechanically separated catalytic volume to a recirculation pump. The recirculation pump may be configured for recirculating a first portion of the alkylate stream from the recirculation pump to a deisobutanizer and a second portion of the alkylate stream to the first mechanically separated catalytic volume to maintain a desired ratio of isobutane to olefins. In certain embodiments, this ratio ranges from about 300:1 to about 500:1. The first portion of the alkylate stream can be directed from the recirculation pump to the deisobutanizer of certain embodiments to separate the first portion of the alkylate stream into (i) the recycle isobutane stream to supply to the first mechanically separated catalytic volume; (ii) the normal butane stream; and (iii) the product stream containing a mixture of high-octane, branched-chain paraffinic hydrocarbons. The recycle isobutane stream may then be directed to the first alkylation zone in the first mechanically separated catalytic volume to alkylate with the isobutane inlet stream and each olefin-containing stream.

While FIG. 1 and FIG. 2 are illustrations with only one multi-zone alkylation reactor, embodiments of the alkylation systems include two, three, or more such reactors. For example, the two or more multi-zone alkylation reactors may be arranged and connected in parallel with one another. In certain embodiments, a single inlet stream may be split and provided to each multi-zone alkylation reactor, either before or after being combined with recycled isobutane. Moreover, in certain embodiments, an outlet stream may be received from each multi-zone alkylation reactor and combined, either before or after splitting an isobutane-rich stream from the outlet stream. In certain embodiments, each reactor can run on a 24-hour cycle length and a feed isobutane to olefin ratio may range from about 5 mol/mol to about 10 mol/mol, which may be measured before a feed stream is provided to the two or more multi-zone alkylation reactors. A bed isobutane to olefin ratio may range between 300 mol/mol and 500 mol/mol, as discussed above. Alkylation reaction conditions may include a temperature of about 40-80° C. and a pressure of about 232-363 psi(g). This temperature range may desirably favor alkylation over polymerization reactions.

Embodiments may also include methods for regenerating an alkylation zone of a multi-zone alkylation reactor. In one such embodiment, a multi-zone alkylation reactor includes two mechanically separated catalytic volumes with a first and a second plurality of alkylation zones that may be loaded with spent alkylation catalysts. The multi-zone alkylation reactor may include a first plurality of conduits configured for fluid flow in a first mechanically separated catalytic volume and a second plurality of conduits configured for fluid flow through in a second mechanically separated catalytic volume. As described above, fluid flow through the first plurality of alkylation zones of the first mechanically separated catalytic volume may be provided in an upward or a downward direction. Similarly, fluid flow through the second plurality of alkylation zones of the second mechanically separated catalytic volume may be provided in an upward or a downward direction. One such method may include (i) directing a regeneration stream to a compressor to produce a compressed regeneration stream. In certain embodiments, the regeneration stream contains hydrogen-rich gas. The hydrogen-rich gas may contain about 60 wt. % to about 90 wt. %, or about 70 wt. % to about 90 wt. %, or about 75 wt. % to about 85 wt. %, or about 70 wt. %, or about 80 wt. % of hydrogen. In certain embodiments, the regeneration stream may contain other components, such as helium or ozone or oxygen. The method may also include (ii) supplying the compressed regeneration stream to a heat exchanger positioned to crossflow the compressed regeneration stream with a spent regeneration stream from an outlet from a multi-zone alkylation reactor to produce a hot compressed regeneration stream and a cooled spent regeneration stream. The method may further include (iii) directing the hot compressed regeneration stream from the heat exchanger to a heater, thereby producing a regeneration feed stream. In certain embodiments, the heater is a fired heater. Additionally, the method may also include (iv) supplying the regeneration feed stream to an inlet of the multi-zone alkylation reactor and (v) directing the regeneration feed stream through the first plurality of alkylation zones in the first mechanically separated catalytic volume and through the second plurality of alkylation zones in the second mechanically separated catalytic volume. This flow may facilitate interaction with the spent alkylation catalyst in the first and second plurality of alkylation zones under catalyst regeneration conditions to regenerate the spent alkylation catalyst. The flow may additionally produce a regenerated catalyst having substantially increased alkylation activity and a spent regeneration stream exiting at an outlet of the multi-zone alkylation reactor. The term "substantially" means an increase in activity of a spent catalyst composition by at least about 50%, or at least about 60%, or at least about 70 wt. %, or at least about 80 wt. %, or at least about 90 wt. %, at least about 95 wt. %, at least about 97 wt. %, or at least about 99 wt. %, or more. In certain embodiments, the regenerated catalyst may have activity similar to a fresh catalyst. The method may additionally include (vi) supplying the spent regeneration stream from the outlet of the multi-zone alkylation reactor to the heat exchanger and (vii) directing the spent regeneration stream from the heat exchanger to a vapor-liquid separator. The vapor-liquid separator may separate spent material of the cooled spent regeneration stream to produce the regeneration stream and a spent material stream. In certain embodiments, the catalyst regeneration conditions may include a temperature up to 275° C. and a pressure of about 290 psi(g).

Figure 3:
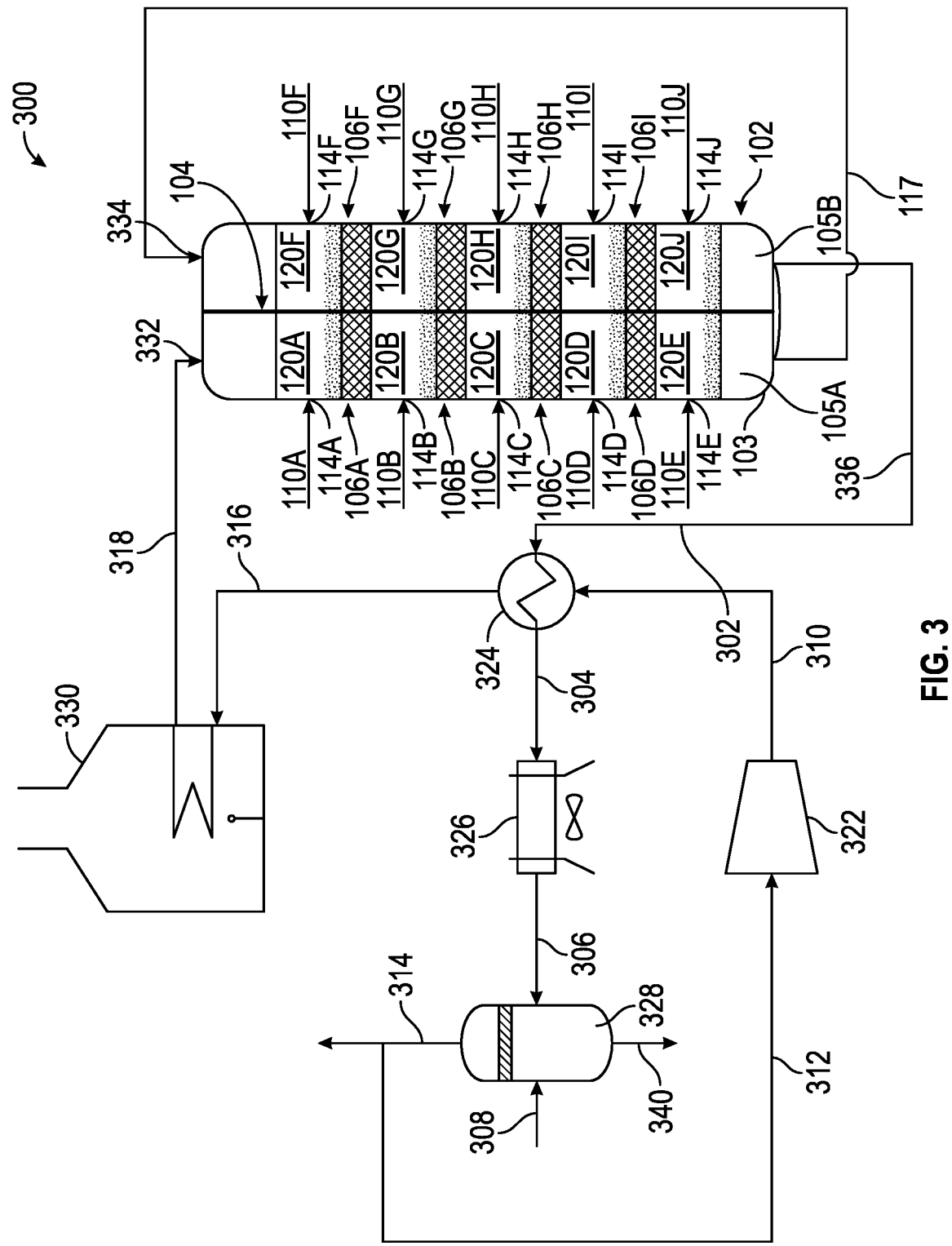
FIG. 3 is a diagrammatic representation of an alkylation system including a multi-zone alkylation reactor coupled to several components, including a heat exchanger, a cooler, a flash drum, a compressor, and a heater, according to an embodiment of the disclosure.

FIG. 3 is a diagrammatic representation of an embodiment of an alkylation system 300 including a multi-zone alkylation 102 reactor coupled to several components. The components may include one or more of a heat exchanger, a cooler, a flash drum, a compressor, and/or a heater, which constitute a regeneration system, according to an embodiment of the disclosure. In the illustrated embodiment, the alkylation system 300 includes a compressor 322, a heat exchanger 324, a cooler 326, a vapor-liquid separator 328, and a heater 330. In certain embodiments, the heater is a fired heater. These and/or other suitable components may be utilized for regenerating one or more alkylation zones 120 of the multi-zone alkylation reactor 102. In the present embodiment, the compressor 322 receives a regeneration stream 312. The compressor 322 is a suitable compression device configured for compressing the regeneration stream 312 to produce a compressed regeneration stream 310. In certain embodiments, the regeneration stream 312 contains about 60 wt. % to about 90 wt. % of hydrogen. In certain embodiments, regeneration pressure of the compressed regeneration stream 310 may be based on regeneration gas purity. The regeneration pressure of some embodiments may be selected to meet a minimum or a target $H_2$ partial pressure threshold, such as about 150-180 psi(g), at reactor outlet to enable effective regeneration operation. The heat exchanger 324 may receive the compressed regeneration stream 310 from the compressor 322. The heat exchanger 324 of the present embodiment may be configured for crossflowing the compressed regeneration stream 310 with a spent regeneration stream 336 from an outlet of a multi-zone alkylation reactor 102, thereby producing a hot compressed regeneration stream 316 and a cooled spent regeneration stream 304. The heat exchanger 324 of other embodiments may implement counterflow or parallel flow between the compressed regeneration stream 310 and the spent regeneration stream 336. The heater 330 may receive the hot compressed regeneration stream 316 from the heat exchanger 324 and heat the hot compressed regeneration stream 316 to produce a regeneration feed stream 318. In certain embodiments, the regeneration feed stream 318 is heated to 275° C. In certain embodiments, the heater is a fired heater. In the illustrated embodiment, a first inlet 332 of the multi-zone alkylation reactor 102 receives the regeneration feed stream 318. The multi-zone alkylation reactor 102 may include the two or more mechanically separated catalytic volumes 105 separated by the one or more vertical partitions 104. The mechanically separated catalytic volumes 105 may include a first plurality of alkylation zones (120A, 120B, 120C, 120D, and 120E) and a second plurality of alkylation zones (120F, 120G, 120H, 120I, and 120J), which are loaded with spent alkylation catalysts. A first plurality of conduits 106A, 106B, 106C, and 106D are configured for downward fluid flow of the regeneration feed stream 318 from alkylation zone 120A and through alkylation zones 120B, 120C, 120D, and 120E in the first mechanically separated catalytic volume 105A. In certain embodiments, the regeneration feed stream 318 interacts with the spent alkylation catalyst in the first plurality of alkylation zones under catalyst regeneration conditions. This interaction may regenerate the spent alkylation catalyst and produce a regenerated catalyst having substantially increased alkylation activity. During regeneration within the multi-zone alkylation reactor 102, soft coke deposited on the catalyst may be removed by the regenerative feed stream 318.

A first alkylate product conduit 117 is configured to receive the regeneration feed stream 318 from the last alkylation zone 120E in the first mechanically separated catalytic volume 105A and direct the regeneration feed stream 318 to a second inlet 334 of the multi-zone alkylation reactor 102. The first alkylation zone 120F in the second mechanically separated catalytic volume 105B may receive the regeneration feed stream 318 from the second inlet 334. A second plurality of conduits 106E, 106F, 106G, and 106H are configured for downward fluid flow of the regeneration feed stream 318 from alkylation zone 120F and through alkylation zones 120G, 120H, 120I, and 120J in the second mechanically separated catalytic volume 105B. As such, the regeneration feed stream 318 flows through the second plurality of alkylation zones 120F, 120G, 120H, 120I, and 120J and the second plurality of conduits 106F, 106G, 106H, and 106I to facilitate interaction with the spent alkylation catalyst therein under catalyst regeneration conditions to regenerate the spent alkylation catalyst and to produce a regenerated catalyst having substantially increased alkylation activity and a spent regeneration stream 336. The catalyst regeneration conditions within the multi-zone alkylation reactor 102 include a temperature up to 275° C. and a pressure of about 290 psi(g), in certain embodiments. In some embodiments, the catalyst regeneration uses reformer grade hydrogen. The spent regeneration stream 336 may exit at an outlet of the multi-zone alkylation reactor 102. The heat exchanger 324 may receive the spent regeneration stream 336 from the outlet of the multi-zone alkylation reactor 102 and produce the cooled spent regeneration stream 304. In some embodiments, the cooler 326 can receive the cooled spent regeneration stream 304 from the heat exchanger 324 and further cool the cooled spent regeneration stream 304 to produce a second cooled spent regeneration stream 306. The vapor-liquid separator 328 may receive the cooled spent regeneration stream 304 from the heat exchanger 324 and/or receive the second cooled spent regeneration stream 306 from the cooler 326. The vapor-liquid separator 328 can be a flash drum, in certain embodiments. In certain embodiments, the vapor-liquid separator 328 can also receive a liquid hydrocarbon stream 308. The vapor-liquid separator 328 may separate spent material, such as C1-C4 hydrocarbons, from the cooled spent regeneration stream 304 and/or the second cooled spent regeneration stream 306 to produce a substantially pure hydrogen stream 314 from which the regeneration stream 312 may be drawn or separated. The vapor-liquid separator 328 may also produce a spent material stream 340 containing materials to be removed, such as C1-C4 hydrocarbons. Thus, the regeneration stream 312 may be decontaminated and regenerated for further use within the alkylation system 300.

Figure 4:
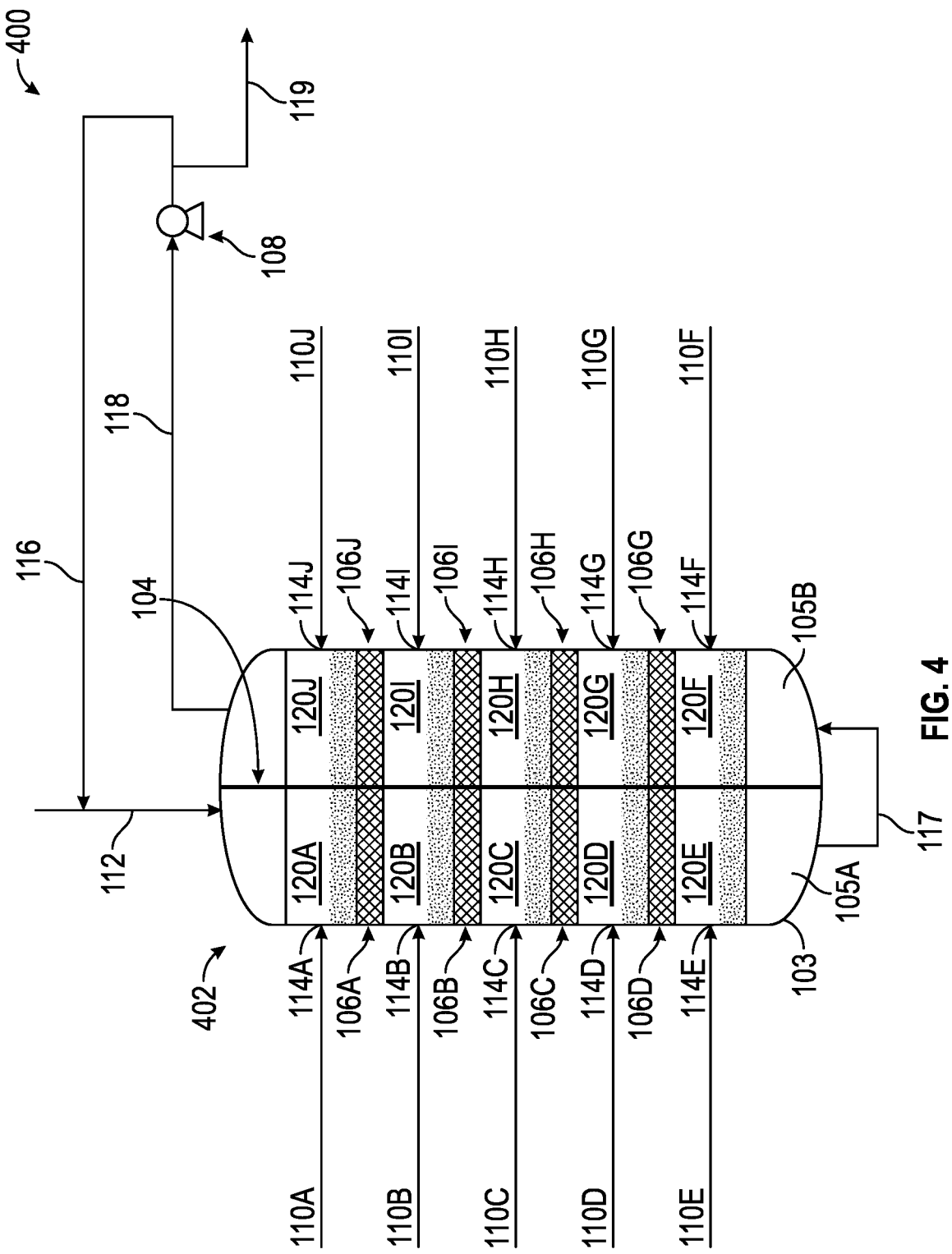
FIG. 4 is an illustrative diagram of a multi-zone alkylation system, according to an embodiment of the disclosure.

FIG. 4 is an illustrative diagram of an alkylation system 400 containing a multi-zone alkylation reactor 402. While certain other embodiments have been described in the preceding figures as having downward flow through each of the mechanically separated catalytic volumes 105, the multi-zone alkylation reactor 402 provides a downward fluid flow in a first mechanically separated catalytic volume 105A and an upward fluid flow in a second mechanically separated catalytic volume 105B. Certain other components of the multi-zone alkylation reactor 402 may generally correspond to the multi-zone alkylation reactor 102 of FIG. 1, where corresponding elements may be described with reference to their operation within the alkylation system 400. For example, the multi-zone alkylation reactor 402 of the present embodiment contains a plurality of alkylation zones 120, such as alkylation zones 120A, 120B, 120C, 120D, 120E, 120F, 120G, 120H, 120I, and 120J, which may be defined within a shell 103 and spaced vertically in a series configuration. At least one vertical partition 104 separates the plurality of alkylation zones 120 into at least the first mechanically separated catalytic volume 105A and the second mechanically separated catalytic volume 105B. A plurality of olefinic feed inlets 114, such as olefinic feed inlets 114A, 114B, 114C, 114D, 114E, 114F, 114G, 114H, 114I, and 114J may be positioned to supply an olefin-containing stream 110 to each of the plurality of alkylation zones 120 in the two mechanically separated catalytic volumes 105A and 105B. An isobutane stream 112 is provided to a first alkylation zone 120A in a first mechanically separated catalytic volume 105A. In the present embodiment, the multi-zone alkylation reactor 102 includes a plurality of conduits 106 to direct fluid flow of the alkylate stream through at least a portion of the plurality of alkylation zones 120. For example, the alkylate stream within alkylation zone 120A may flow sequentially through conduit 106A, alkylation zone 120B, conduit 106B, alkylation zone 120C, conduit 106C, alkylation zone 120D, conduit 106D, and alkylation zone 120E. The first plurality of conduits 106A, 106B, 106C, and 106D may be configured to provide downward fluid flow of the alkylate stream from alkylation zone 120A through alkylation zones 120B, 120C, 120D, and 120E in the first mechanically separated catalytic volume 105A.

A first alkylate product conduit 117 may transport the alkylate stream from a last alkylation zone 120E in the first mechanically separated catalytic volume 105A to a first alkylation zone 120F in the second mechanically separated catalytic volume 105B. In the present embodiment, the first alkylation zone 120F is a lowermost alkylation zone of the second mechanically separated catalytic volume 105B. As such, a second plurality of conduits 106F, 106G, and 106H, and 106I may be configured to provide upward fluid flow of the alkylate stream from alkylation zone 120F through alkylation zones 120G, 120H, 120I, and 120J in the second mechanically separated catalytic volume 105B. For example, the alkylate stream within alkylation zone 120F may flow sequentially through conduit 106F, alkylation zone 120G, conduit 106G, alkylation zone 120H, conduit 106H, alkylation zone 120I, conduit 106I, and alkylation zone 120J. A second alkylate product conduit 118 may transport the alkylate stream from a last alkylation zone 120J in the second mechanically separated catalytic volume 105B to a recirculation pump 108.

Accordingly, the alkylation system 400 provides downward fluid flow in the first mechanically separated catalytic volume 105A and upward fluid flow in the second mechanically separated catalytic volume 105B. In certain embodiments, this mixed or combination flow direction arrangement of the alkylation system 400 enables a reduced or optimized length of conduits or piping (e.g., including the first alkylate product conduit 117 and/or the second alkylate product conduit 118), compared to embodiments having downward fluid flow in each mechanically separated catalytic volume 105 or embodiments having upward fluid flow in each mechanically separated catalytic volume 105.

When ranges are disclosed herein, ranges from any lower limit may be combined with any upper limit to recite a range not explicitly recited, as well as ranges from any lower limit may be combined with any other lower limit to recite a range not explicitly recited, in the same way, ranges from any upper limit may be combined with any other upper limit to recite a range not explicitly recited. Additionally, reference to values stated in ranges includes each and every value within that range, even though not explicitly recited. Thus, every point or individual value may serve as its own lower or upper limit combined with any other point or individual value or any other lower or upper limit, to recite a range not explicitly recited.

In the drawings and specification, several embodiments of systems and involving a multi-zone alkylation reactor have been disclosed. Although specific terms are employed, the terms are used in a descriptive sense only and not for purposes of limitation. Embodiments of systems and methods have been described in considerable detail with specific reference to the illustrated embodiments. However, it will be apparent that various modifications and changes may be made within the spirit and scope of the embodiments of systems and methods as described in the foregoing specification, and such modifications and changes are to be considered equivalents and part of this disclosure.

What is claimed is:

1. An alkylation system comprising:
a multi-zone alkylation reactor comprising:
  a plurality of alkylation zones spaced vertically in a series configuration;
  at least one vertical partition splitting the plurality of alkylation zones into at least a first mechanically separated catalytic volume and a second mechanically separated catalytic volume;
  an isobutane inlet positioned to supply an isobutane stream to the first mechanically separated catalytic volume;
  at least one olefinic feed inlet positioned to supply an olefin-containing stream to the plurality of alkylation zones, the olefin-containing stream reacting with the isobutane stream to produce an alkylate stream; and
  a first alkylate product conduit to transport the alkylate stream from the first mechanically separated catalytic volume to the second mechanically separated catalytic volume.

2. The alkylation system of claim 1, wherein the multi-zone alkylation reactor comprises:
  a first plurality of conduits interconnecting each alkylation zone of the plurality of alkylation zones in the first mechanically separated catalytic volume; and
  a second plurality of conduits interconnecting each alkylation zone of the plurality of alkylation zones in the second mechanically separated catalytic volume.

3. The alkylation system of claim 1, wherein the plurality of alkylation zones is configured to direct the alkylate stream in a downward flow direction in each of the first mechanically separated catalytic volume and the second mechanically separated catalytic volume.

4. The alkylation system of claim 1, wherein the plurality of alkylation zones is configured to direct the alkylate stream in an upward flow direction in at least one of the first mechanically separated catalytic volume and the second mechanically separated catalytic volume.

5. The alkylation system of claim 1, wherein each of the first mechanically separated catalytic volume and the second mechanically separated catalytic volume is a hydraulically sealed reaction chamber.

6. The alkylation system of claim 1, wherein the at least one olefinic feed inlet comprises a plurality of olefinic feed inlets configured to supply the olefin-containing stream to each alkylation zone of the plurality of alkylation zones.

7. The alkylation system of claim 1, wherein the first alkylate product conduit is configured to transport the alkylate stream from a last alkylation zone in the first mechanically separated catalytic volume to a first alkylation zone in the second mechanically separated catalytic volume, and wherein the multi-zone alkylation reactor comprises a second alkylate product conduit to transport the alkylate stream from a last alkylation zone in the second mechanically separated catalytic volume.

8. The alkylation system of claim 7, wherein the second alkylate product conduit is configured to transport the alkylate stream to a recirculation pump.

9. The alkylation system of claim 8, comprising the recirculation pump, wherein the recirculation pump is configured to:
  receive the alkylate stream from the second alkylate product conduit;
  direct a first portion of the alkylate stream for further processing to produce an enriched alkylate product containing high-octane, branched-chain paraffinic hydrocarbons; and
  recirculate a second portion of the alkylate stream to the first mechanically separated catalytic volume, thereby maintaining a ratio of isobutane to olefin in the multi-zone alkylation reactor ranging from about 300:1 to about 500:1.

10. The alkylation system of claim 8, comprising the recirculation pump, wherein the recirculation pump is configured to:
  receive the alkylate stream from the second alkylate product conduit;
  direct a first portion of the alkylate stream to a deisobutanizer; and
  recirculate a second portion of the alkylate stream to the first mechanically separated catalytic volume, thereby maintaining a ratio of isobutane to olefin in the multi-zone alkylation reactor ranging from about 300:1 to about 500:1.

11. The alkylation system of claim 10, comprising the deisobutanizer, wherein the deisobutanizer is configured to separate the first portion of the alkylate stream from the recirculation pump into:
  a recycle isobutane stream to supply to the first mechanically separated catalytic volume;
  a n-butane stream; and
  a product stream containing high-octane, branched-chain paraffinic hydrocarbons.

12. The alkylation system of claim 1, wherein the multi-zone alkylation reactor comprises at least two vertical partitions that define three mechanically separated catalytic volumes.

13. The alkylation system of claim 12, wherein the multi-zone alkylation reactor comprises a second alkylate product conduit configured to transport the alkylate stream from the second mechanically separated catalytic volume to a third mechanically separated catalytic volume.

14. A method for production of an alkylate, the method comprising:
  supplying an isobutane stream to a multi-zone alkylation reactor, the multi-zone alkylation reactor having at least one vertical partition defining: a first mechanically separated catalytic volume comprising a first plurality of alkylation zones, and a second mechanically separated catalytic volume comprising a second plurality of alkylation zones;
  supplying an olefin-containing stream through at least one olefinic feed inlet to the first plurality of alkylation zones and the second plurality of alkylation zones to produce an alkylate stream; and
  directing the alkylate stream from the first plurality of alkylation zones through a first alkylate product conduit to the second plurality of alkylation zones.

15. The method of claim 14, further comprising:
  directing the alkylate stream from the second plurality of alkylation zones through a second alkylate product conduit to a recirculation pump; and
  recirculating a portion of the alkylate stream from the recirculation pump to the first mechanically separated catalytic volume, thereby maintaining a ratio of isobutane to olefin in the multi-zone alkylation reactor ranging from about 300:1 to about 500:1.

16. The method of claim 14, further comprising:
  directing the alkylate stream through the first plurality of alkylation zones in a downward flow direction; and
  directing the alkylate stream through the second plurality of alkylation zones in the downward flow direction.

17. The method of claim 14, further comprising:
  directing the alkylate stream through the first plurality of alkylation zones in a downward flow direction; and
  directing the alkylate stream through the second plurality of alkylation zones in an upward flow direction.

18. A method for regenerating an alkylation zone of a multi-zone alkylation reactor, the method comprising:
  supplying a regeneration feed stream to an inlet of a multi-zone alkylation reactor, the multi-zone alkylation reactor having a vertical partition defining:
    a first mechanically separated catalytic volume comprising a first plurality of alkylation zones, and
    a second mechanically separated catalytic volume comprising a second plurality of alkylation zones;
  directing the regeneration feed stream through the first mechanically separated catalytic volume and through the second mechanically separated catalytic volume to regenerate spent alkylation catalyst therein by producing a regenerated catalyst having substantially increased alkylation activity and a spent regeneration stream; and
  directing the spent regeneration stream out of an outlet of the multi-zone alkylation reactor.

19. The method of claim 18, comprising producing the regeneration feed stream by:
  directing a regeneration stream containing at least 60 weight percent of hydrogen to a compressor to produce a compressed regeneration stream;
  supplying the compressed regeneration stream to a heat exchanger positioned to crossflow the compressed regeneration stream with the spent regeneration stream from the multi-zone alkylation reactor to produce a hot compressed regeneration stream and a cooled spent regeneration stream; and
  directing the hot compressed regeneration stream from the heat exchanger to a heater to produce the regeneration feed stream.

20. The method of claim 19, comprising:
  supplying the spent regeneration stream from the multi-zone alkylation reactor to the heat exchanger; and
  directing the cooled spent regeneration stream from the heat exchanger to a vapor-liquid separator to separate spent material from the cooled spent regeneration stream to produce the regeneration stream and a spent material stream.

* * * * *